United States Patent [19]

Ryder et al.

[11] Patent Number: 5,186,317
[45] Date of Patent: Feb. 16, 1993

[54] LENS CASE FOR CONTACT LENS DISINFECTING SYSTEM

[75] Inventors: Francis E. Ryder, Arab; Rowland W. Kanner, Guntersville, both of Ala.

[73] Assignee: Ryder International Corporation, Arab, Ala.

[21] Appl. No.: 830,887

[22] Filed: Feb. 4, 1992

[51] Int. Cl.⁵ .................... B65D 85/38; A61L 2/18
[52] U.S. Cl. .................... 206/5.1; 134/901; 422/301
[58] Field of Search .......... 422/102, 300, 301, 310; 206/5.1; 220/608, 633, 635, 636; 215/1 C; 134/137, 143, 901

[56] References Cited

U.S. PATENT DOCUMENTS

| | | | |
|---|---|---|---|
| D. 269,158 | 5/1983 | Gaunt | 215/1 C X |
| 3,770,113 | 11/1973 | Thomas . | |
| 3,977,551 | 8/1976 | Ciarico | 215/1 C |
| 3,978,232 | 8/1976 | Dodsworth et al. | 215/1 C X |
| 4,200,187 | 4/1980 | Thomas . | |
| 4,396,583 | 8/1983 | LeBoeuf | 134/901 X |
| 4,637,919 | 1/1987 | Ryder et al. . | |
| 4,700,729 | 10/1987 | Thaler | 134/901 |
| 4,721,124 | 1/1988 | Tuerheimer et al. | 206/5.1 X |
| 4,807,750 | 2/1989 | Ryder et al. | 206/5.1 |
| 4,890,729 | 1/1990 | Ranalletta | 206/5.1 |
| 4,981,657 | 1/1991 | Ryder | 422/310 |
| 5,089,240 | 2/1992 | Perlaky . | |
| 5,101,967 | 4/1992 | Sibley | 206/5.1 |

*Primary Examiner*—Bryon P. Gehman
*Attorney, Agent, or Firm*—Trexler, Bushnell, Giangiorgi & Blackstone, Ltd.

[57] ABSTRACT

A contact lens case for use with a contact lens disinfecting system employing one or more disinfecting tablets or catalysts and which comprises a cup having a bottom portion and a basket assembly for releasably holding contact lenses insertable into the cup. The cup is of dimentions sufficient for holding a predetermined amount of disinfecting fluid in disinfecting contact with the lenses when the basket assembly is inserted into the cup. A reaction chamber of predetermined dimensions for retaining the disinfecting tablets in close proximity within the cup for permitting occurrence of disinfecting solution-producing reactions depends from the bottom portion of said cup. There is also provided a novel, one-piece basket assembly including a cap, stem, base plate, hingedly connected baskets and latching extensions.

22 Claims, 2 Drawing Sheets

LENS CASE FOR CONTACT LENS DISINFECTING SYSTEM

BACKGROUND AND SUMMARY OF THE INVENTION

The present invention relates generally to a unique construction or a lens case for use with contact lenses, and, more specifically, to a lens case having particular utility with a disinfecting system employing one or more tablets in a liquid medium, such as a sterilizing solution.

Given the inconvenience and the perceived cosmetically negative effect of eye glasses, many people, especially younger ones, are choosing to obtain contact lenses in lieu of eye glasses. Contact lenses are also used to change a person's eye color. Accordingly, contact lenses have become quite popular and are extensively used by many persons in modern society. Contact lenses, however, must be used carefully if they are to be effective, and if the wearer's eyes are not to be damaged or harmed in any way by the lenses.

Because contact lenses are worn directly on the eye itself, the lenses are constantly subject to the wearer's tears. These tears, and other bodily fluids common to the eye, bear proteins which can be deposited on the surface of the contact lenses. Additionally, the eyes are always subject to contaminants, gaseous, liquid, and particulate in nature, which also can be deposited on the surface of the contact lenses.

Once these deposits build up on the lenses to a sufficient degree, the lenses must be removed from the wearer's eyes and disinfected. For some types of contact lenses, this disinfecting is recommended on a daily basis. Additionally, the contact lenses are often subjected to a enzymatic bath, usually weekly, for loosening and removing protein deposits on the surface of the lenses.

If disinfecting and cleanings are not done, and done properly, serious eye infections and injuries, possibly accompanied by loss of vision, can occur. Thus, it is necessary for a wearer to properly maintain the contact lenses, in accordance with manufacturer's and a doctor's instructions.

When the contact lenses are removed from the eyes of the wearer and cleaned, or subjected to any type of contaminant, the lenses must be sterilized or disinfected before they are inserted back into the eyes. If the lenses are not disinfected, the lenses may transmit an infection to the wearer's eyes. Accordingly, it is necessary to properly and thoroughly disinfect the contact lenses before a wearer inserts them into his or her eyes.

The lens case, constructed according to the teachings of the present invention, is intended to solve some of the problems inherent in the lens cases of the prior art. The lens case of the invention is specifically intended for use with a contact lens disinfecting system that employs one or more tablets or catalysts in a liquid medium.

In this regard, there exist in the market contact lens disinfecting systems wherein one or more tablets or similar components are disposed within a liquid medium to produce a chemical lens disinfecting reaction. One common well known system employs a weak solution of hydrogen peroxide, approximately three percent, and a catalyst which is introduced into the solution and decomposes the hydrogen peroxide. There are also in development certain proprietary disinfecting systems which will employ the disposition of one or more tablets in a liquid medium, and rely upon a decomposition or effervescence of the tablet or tablets to produce the desired chemical reaction. In both of the above types of disinfecting systems, it is preferred to maintain the tablets or catalysts in the lower region of the container and to prevent the tablets or catalysts from migrating to the upper level of the liquid in order to promote a more efficient chemical reaction and to attain the desired, predetermined exposure of the lenses to the disinfecting medium.

With the hydrogen peroxide reduction system noted above, and the one or multiple tablet systems, there is a problem of the catalyst or tablet floating to the surface of the liquid medium. In this regard, the decomposition of the hydrogen peroxide results in the production of oxygen bubbles which can adhere to the catalyst and cause it to become buoyant. The single or multiple tablet systems may rely upon a effervescence-type tablet and disintegration which can render the tablets buoyant before they have completely dissolved. Also, with a multiple tablet system, it is necessary that the tablets be kept in close proximity as they decompose. To the best of the Applicants knowledge, the type of lens cases employed in the prior art do not address the problem of tablets or catalyst elements becoming buoyant and floating or migrating to the upper level of the liquid medium, which can result in a less efficient lens disinfection procedure. The present invention, as explained in greater detail hereinafter, provides a simple and economical means for preventing such action and also for maintaining a plurality of tablets not only submerged in the liquid, but in close proximity.

OBJECTS AND SUMMARY OF THE INVENTION

A general object of the present invention is to provide a unique lens case for contact lenses.

A more specific object of the invention is to provide a lens case for a disinfecting system wherein tablets or catalyst elements used in the system are maintained in a submerged, juxtaposed position.

Yet another more specific object of the invention is to provide a lens case having particular utility with a multiple tablet disinfecting system.

Another object of the present invention is to provide a lens case which eliminates pockets where contaminants can reside, thereby insuring proper disinfection of contact lenses.

An additional object of the invention is to provide a lens case having a construction which promotes fluid flow around contact lenses, and drainage of fluid from said lenses.

A further object of the present invention is to provide a lens case which safely accommodates pressures generated therein by effervescence of cleaning and/or disinfecting tablets.

Another object of the invention is to provide a lens case which promotes migration of tablets or catalysts to a bottom of the case.

An additional object of the present invention is to provide a lens case which maintains multiple tablets or catalysts in close proximity therein to facilitate occurrence of any chemical reactions therebetween.

A further object of the invention is to provide a lens case which permits aggitation of disinfecting solutions therein to promote proper disinfection of contact lenses from the case.

A contact lens case, constructed according to the teachings of the present invention, for use with a contact lens disinfecting system employing one or more tablets or catalysts and which comprises a cup having a bottom portion and a basket assembly for releasably holding a pair of contact lenses insertable into the cup. The cup is of dimensions sufficient for holding a predetermined amount of disinfecting liquid or liquid medium in contact with the lenses when the basket assembly is inserted into the cup. A reaction chamber of predetermined dimensions for retaining the disinfecting system tablets or catalysts in close proximity within the cup for permitting occurrence of disinfecting fluid-producing reactions depends from the bottom portion of the cup. A novel basket assembly for storing the lenses is also proved.

BRIEF DESCRIPTION OF THE DRAWINGS

The organization and manner of the structure and operation of the invention, together with further objects and advantages thereof, may best be understood by reference to the following description taken in connection with the accompanying drawings, wherein like reference numerals identify like elements in which.

DETAILED DESCRIPTION OF THE PREFERRED EMBODIMENT

While the invention may be susceptible to embodiment in different forms, there is shown in the drawings, and herein will be described in detail, a specific embodiment with the understanding that the present disclosure is to be considered an exemplification of the principles of the invention, and is not intended to limit the invention to that as illustrated and described herein.

Figures 1, 2:
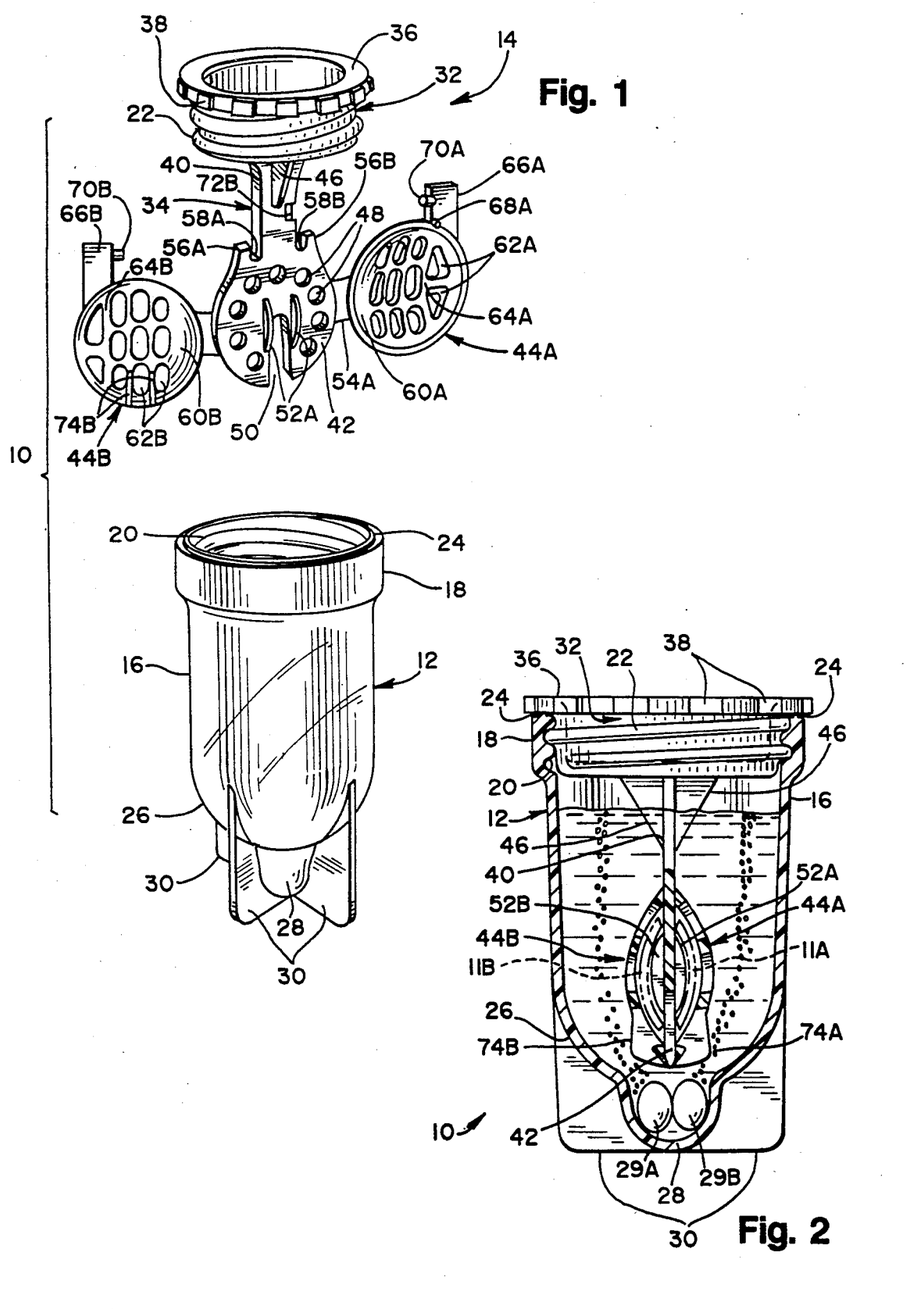
FIG. 1 is an exploded perspective view of a lens case including cup and a basket structure, with baskets of the basket structure open, and constructed according to the teachings of the present invention.
FIG. 2 is an assembled sectional view of the lens case of FIG. 1 showing one or more tablets or catalysts in a reaction chamber.

Referring initially to FIG. 1, a unique contact lens case 10, constructed according to the teachings of the present invention, and having particular utility with a disinfecting system for contact lenses 11A and 11B which uses one or more tablets or catalysts, is illustrated in exploded perspective form. The lens case 10 is preferably constructed of a suitable plastic material, however, other materials can also be used. The lens case 10 generally comprises a cup 12 and a basket assembly 14 removably attached to the cup 12. The basket assembly 14 can be, and is preferably molded as a single component.

The structure and configuration of the cup 12 is shown in FIGS. 1 and 2. The cup 12 has a hollow substantially cylindrical body 16 having a relatively enlarged upper end portion 18 having internal threads 20. The the cup 12 is able to hold disinfecting fluid, or other fluids necessary for the proper care of the contact lenses 11A and 11B depending upon the particular lens disinfecting system with which the lens case 10 is to be used. Therefore, the volume enclosed by the cup 12 is predetermined such that the volume is sufficient to retain the required amount of fluid for disinfection of the lenses 11A and 11B. Also, the volume of the cup 12 is chosen so that a substantial volume of dead air space may be disposed above an upper level of the fluid when the basket assembly 14 is assembled to accommodate any gases liberated by effervescence of the disinfecting tablets, as discussed above.

The threads 20 are constructed for operatively meshing with external threads 22 on the basket assembly 14 when the basket assembly 14 is inserted into the cup 12. When the threads 20 and 22 are properly intermeshed, they served to seal the volume of the cup 12, thereby preventing spillage of the fluid, as well as spattering thereof under the influence of gases generated by effervescence of the disinfecting tablets or catalysts.

To further insure against such spillage and spattering, a sealing ridge 24 is located on a distal surface of the upper end portion 18. The sealing ridge 24 projects upwardly a certain distance from the distal surface of the portion 18 and preferably extends around the entire circumference of the portion 18. When the basket assembly 14 is applied to the cup 12, the ridge 24 is compressed therebetween sufficiently to provide a seal, thereby preventing spillage and spattering.

The cup 12 also has a novel, uniquely constructed bottom portion 26. The bottom portion 26 depends from the body 16 and has a radiused surface, as illustrated in FIGS. 1 and 2. The bottom portion 26 slopes downwardly and inwardly to define or provide a depending reaction chamber 28, which is also radiused. However, it is to be noted that the radius of the reaction chamber 28 is significantly smaller than the radius of the bottom portion 26. The reduced radius of the reaction chamber 28 allows the disinfecting tablets 29A and 29B to be maintained in close proximity to each other as they effervesce or dissolve, thereby insuring the proper, desired disinfection action. Accordingly, the reaction chamber 28 is dimensioned for maintaining the disinfecting tablets sufficiently close to promote effective disinfection of the contact lenses 11A and 11B by allowing for disinfecting fluid-producing reactions to occur. Also, the basket assembly 14 is configured to overlie the reaction chamber 28 and maintain the tablets 29A and 29B in the desired juxtaposed position. This aspect of the invention will be discussed in greater detail hereinbelow.

The bottom portion 26 and the reaction chamber 28 are radiused, being free of corners, edges and obstructions, thereby insuring that the disinfecting tablets or catalysts, usually in the form of tablets, will travel to and be retained in the reaction chamber 28. In this manner, the cup 12 can be filled to an appropriate, predetermined level with a saline solution, or the like, for disinfecting of the lenses 11A and 11B. Then, the disinfecting tablets can be added to the cup 12. These tablets will, under the influence of gravity, move or migrate to the reaction chamber 28, where chemical reactions necessary for disinfection of the lenses 11A and 11B can take place. The body 16 and the bottom portion 26 thusly act as a funnel or guide directing the tablets into the reaction chamber 28.

The substantially smooth configuration of the interior of the cup 12 also insures that the number of stagnant pockets of disinfecting fluid within the cup 12 will be minimized, if not eliminated altogether. This configuration further eliminates pockets within the cup 12 where old disinfecting fluid could reside, thereby facilitating complete drainage of that fluid upon completion of the disinfection process. Because most, if not all of the old disinfecting fluid will be drained from the cup 12, the risk of contamination of new disinfecting fluid is thereby minimized. This provides for a disinfection process having increased effectiveness as compared with prior art disinfection processes utilized in prior art lens cases.

Because the bottom portion 26 and the reaction chamber 28 is radiused, depending exterior integral fins 30 are provided to support the case 10. The fins 30 extend downwardly approximately from a juncture between the body 16 and the bottom portion 26 substantially parallel to a surface defined by the body 16 to a bottom-most portion of the reaction chamber 28. The fins 30 define right angles, and extend from a portion of the body 16, the bottom portion 26, and the reaction chamber 28 for providing support to the cup 12. Due to the right angle configuration of the fins 30, the cup 12 is capable of remaining upright and stationary on any suitably planar surface.

With the structure of the cup 12 being thusly disclosed, the construction of the basket assembly 14 will now be discussed. The basket assembly 14 generally comprises a threaded cap 32 and a basket structure 34 depending from the cap 32. The cap 32 and the structure 34 are preferably provided as a single molded component. The cap 32 is substantially cylindrical in configuration, and includes the external threads 22 for mating with the threads 20 on the cap 32. Accordingly, the cap 32 has a diameter sufficient for allowing meshing and mating of the threads 20 and 22 in order to form an effective threaded seal between the cup 12 and the assembly 14, as noted above.

To further improve the seal between the cup 12 and the assembly 14, the cap 32 includes a flange 36 which extends annularly outward from the threads 22. The flange 36 is thusly annular shaped having a smooth underside. The underside of the flange 36 compressively engages the ridge 24 on the upper end portion 18 of the cup 12 when the assembly 14 is threadibly coupled to the cup 12 for providing further insurance of an effective seal between the cup 12 and the assembly 14 for preventing spillage and spattering.

The cap 32 also has diametrically extending protuberances 38 located along a circumference of the cap 32. In a preferred construction, the protuberances 38 are not located along the entire circumference of the cap 32. The protuberances 38 facilitate gripping of the cap 32, thereby providing for easy manipulation thereof. The protuberances 38 also provide bearing surfaces for accepting a torque applied by a person for rotating the basket assembly 14 to matingly engage and disengage the threads 20 on the cup 12 with the threads 22 on the basket assembly 14. In this manner, a person can apply sufficient torque to the basket assembly 14 to insure a releasable threadibly sealed fit between the the cup 12 and the assembly 14.

Figure 3:
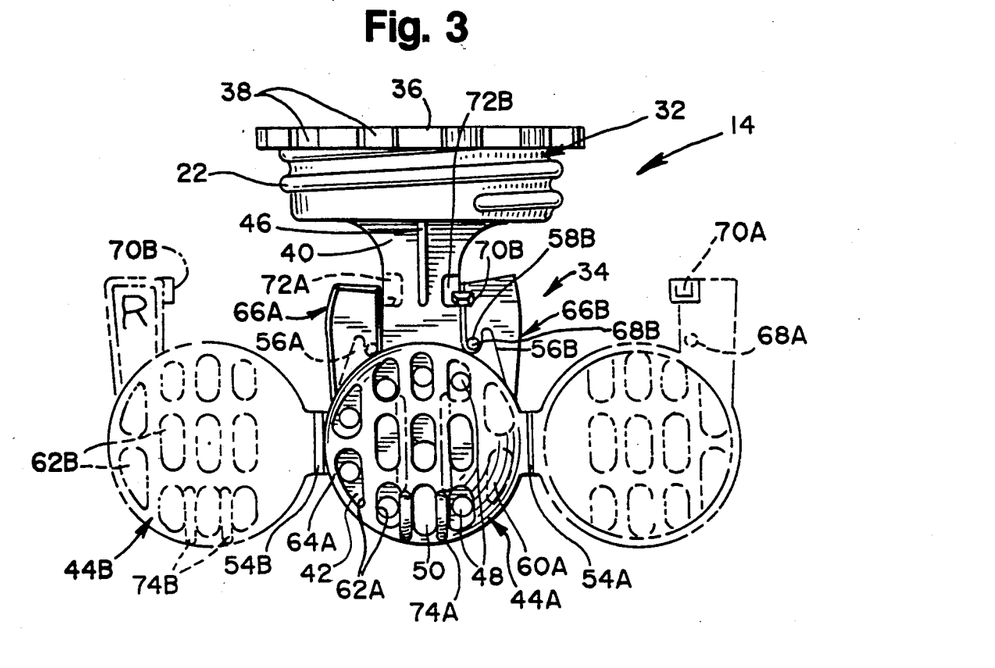
FIG. 3 is an elevational view of the basket assembly of FIG. 1 with the baskets closed, and showing the basket open position in phantom.

The general construction and configuration of the basket structure 34 is illustrated in FIGS. 1 through 3. As shown, the basket structure 34 depends centrally from a side of the cap 32 opposite to the flange 36 substantially perpendicularly to a plane defined by the cap 32. The basket structure 34 generally comprises a stem or leg 40 connected at one end thereof to the cap 32 and at the opposite end thereof to a substantially circular base member 42 bearing hinged baskets 44A and 44B.

A flared portion of the stem or leg 40 is connected to the cap 32 for providing support to the plate 42 and the baskets 44A and 44B. Depending ribs 46 are also connected between the cap 32 and the leg 40 for providing added support to the base plate 42 and the baskets 44A and 44B. The ribs 46 are offset on the cap 32 substantially ninety degrees from the flared portion of the leg 40. In this manner, the leg 40 is fixedly connected to the cap 32. It is to be noted that the basket structure 34 is preferably molded as a single component.

The base plate 42 is attached to the end of the stem 40 opposite to the end thereof connected to the cap 32. The base plate 42 is generally disk shaped, but does include structures which cause said plate 42 to depart from its generally disk shaped configuration. Specifically, the base plate 42 has means for promoting disinfecting fluid flow and drainage in the form of apertures 48 and a vertical slot 50 disposed through the base plate 42. The apertures 48 and the slot 50 allow flow of fluid therethrough and therefrom. In this way, the entirety of the contact lenses 11A and 11B are subjected to the disinfecting fluid, which can flow freely over the lenses 11A and 11B as internal fluid currents are generated, as will be discussed in further detail hereinbelow.

The slot 50 is located along a radius of the base plate 42 substantially parallel to an axis of elongation of the leg 40. The slot 50 extends from the approximate center of the base plate 42 along the entire length of the radius so that the continuity of the circumference of the plate 42 is interrupted by the slot 50. When the basket assembly 14 is properly inserted into the cup 12, the slot 50 opens towards and opposes the reaction chamber 28 so that disinfecting fluid formed within the reaction chamber 28 can move freely about the basket structure 34 and on both sides of the lenses 11A and 11B contained therein through the slot 50. The slot 50 is disposed and dimensioned for promoting maximum fluid flow about both surfaces of the lenses 11A and 11B. The slot 50 also promotes fluid drainage from back sides of the lenses 11A and 11B, thereby facilitating removal thereof from the basket structure by eliminating fluid surface tension.

The slot 50 therefore defines a downwardly directed radius of the plate 42 substantially parallel to the axis of elongation of the leg 40. The apertures 48 are substantially circular in configuration and are distinctly disposed along a circumference of the plate 42 extending from opposite sides of the slot 50. The apertures 48 also promote disinfecting fluid flow around and drainage from the lenses 11A and 11B. The apertures 48 also insure that both surfaces of the lenses 11A and 11B will be subjected to substantially the same amount of fluid flow. This insures appropriate disinfection of the lenses 11A and 11B.

The base plate 42 has means for positively locating the lenses 11A and 11B thereon in the form of a pair of radiused support fins 52A and 52B projecting substantially perpendicularly upwardly from both surfaces of the plate 42. The radius of the support fins 52A and 52B is chosen to be substantially equal to the general radius of curvature of the lenses 11A and 11B. The support fins 52A and 52B are located centrally on the plate 42 and extend vertically along a portion of the slot 50, flanking the slot 50 along opposing sides thereof. The fins 52A and 52B locate the lenses 11A and 11B centrally on the plate 42 for insuring that the entirety of both lenses 11A and 11B is exposed to the disinfecting fluid.

The baskets 44A and 44B are attached by integral hinges 54A and 54B, respectively, to the plate 42 along diametrically opposing sides thereof offset ninety degrees from the side of the plate 42 occupied by the slot 50. The hinges 54A and 54B extend vertically substantially tangentially to the circumference of the plate 42. The hinges 54A and 54B are constructed for allowing shifting of the baskets 44A and 44B between an open position, as illustrated in FIG. 1, and a closed or locked position, as illustrated in FIG. 2 and 3. Specifically, the hinges 54A and 54B are preferably thinner than the plate 42 and the baskets 44A and 44B to provide the required flexibility.

Figure 4:
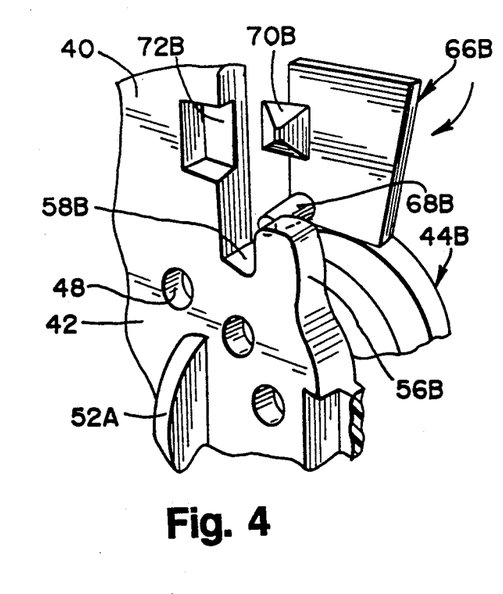
FIG. 4 is an enlarged partial perspective view of a portion of the basket assembly with a basket slightly opened illustrating the construction of the alignment and locking means.
Figure 5:
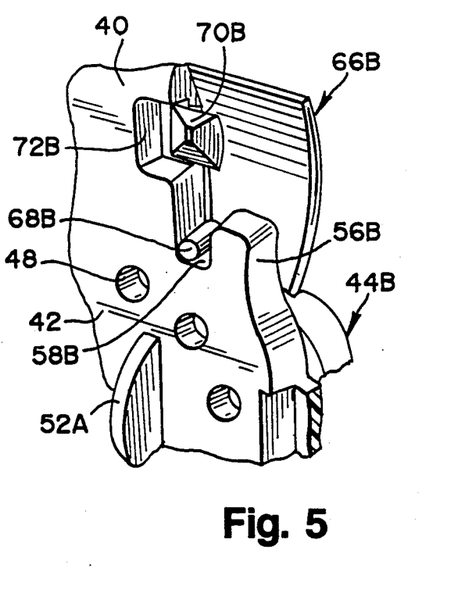
FIG. 5 is a view, similar to that of FIG. 4, with a basket closed.

With reference to FIGS. 1, 4 and 5, alignment means in the form of ears 56A and 56B project upwardly from opposed locations on the base plate 42 generally diametrically opposed to the slot 50 and offset upwardly from the hinges 54A and 54B. The ears 56A and 56B extend from the circumference of the plate 42 and flank the stem or leg 40 in substantially parallel fashion. The ears 56A and 56B define alignment notches 58A and 58B, respectively, located adjacent the ears 56A and 56B and the stem or leg 40 for accepting alignment pins disposed on the baskets 44A and 44B for aligning the baskets 44A and 44B with the plate 42 when the baskets 44A and 44B are in the closed position, FIG. 5. The operation of these structures will be discussed in further detail hereinbelow.

The baskets 44A and 44B are attached to ends of the integral flexible hinges 54A and 54B, respectively, opposite to the ends thereof attached to the base plate 42. The baskets 44A and 44B are substantially circular in configuration and are concaved so that an arc defined by the baskets 44A and 44B opens towards the plate 42 when the baskets 44A and 44B are in the closed position. The hinges 54A and 54B are attached substantially tangentially to the baskets 44A and 44B. The concaved shape of the baskets 44A and 44B is curved so as to accommodate the curvature of the contact lenses 11A and 11B located on the base plate 42 by the support fins 52A and 52B.

The baskets 44A and 44B comprise solid portions 60A and 60B, respectively, located adjacent the hinges 54A and 54B. The solid portions 60A and 60B lend strength and structural integrity to the hinged connection between the plate 42 and the baskets 44A and 44B. In this manner, shifting of the baskets 44A and 44B between the open and closed positions should not compromise the integrity of the hinged connection between the plate 42 and the baskets 44A and 44B.

It is to be noted that the solid portions 60A and 60B do not occupy the entirety of the partially spherical portions of the baskets 44A and 44B. Specifically, the baskets 44A and 44B include arrays of openings 62A and 62B, respectively, which define a large portion of the baskets' surfaces. These openings 62A and 62B represent portions removed from the baskets 44A and 44B for facilitating the flow of disinfecting fluid or solution therethrough to the contact lenses 11A and 11B, as well as drainage of that fluid. The openings 62A and 62B cooperate with the apertures 48 and the slot 50 to insure that the opposed surfaces of the lenses 11A and 11B are exposed to the disinfecting solution.

While the openings 62A and 62B occupy a large portion of the basket surfaces, the structural integrity of the baskets 44A and 44B is not compromised by their presence. Reinforcing arrays in the form of a lattice of ribs 64A and 64B, respectively, are disposed between adjacent openings 62A and 62B for insuring the structural integrity of the baskets 44A and 44B and for protecting the lenses 11A and 11B when the baskets 44A and 44B are in the closed position.

To facilitate shifting of the baskets 44A and 44B between the open and the closed position, or handles or extensions 66A and 66B are provided projecting from the baskets 44A and 44B, respectively, in a substantially vertically upwards fashion. The handles or extensions 66A and 66B are substantially planar in shape, and are preferably thinner than the baskets 44A and 44B so that the handles or extensions 66A and 66B can readily flex with respect to the baskets 44A and 44B. The handles 66A and 66B extend upwardly a sufficient distance to locate distal ends thereof above a latitudinal midline of the stem 40. The handles 66A and 66B have a width sufficient so that interior edges of the handles 66A and 66B facing the hinges 54A and 54B abut opposite edges of the leg 40 when the baskets 44A and 44B are in the closed position.

The extensions 66A and 66B include structures which depart from the generally planar construction thereof. Often, for the convenience of the contact lens wearer, indicia in the form of an "R" and an "L", indicating which eye a particular contact lens 11A or 11B came from, are provided on a side of the extensions 66A and 66B facing apexes of the baskets 44A and 44B. These indicia can be raised from the surface of the handles 66A and 66B to facilitate recognition thereof. In this way, the wearer will be able to distinguish between the two contact lenses 11A and 11B, which, by themselves, are often indistinguishable to an untrained eye.

The extensions 66A and 66B also have other structures which depart from the overall generally planar construction. Specifically, an alignment pin 68A and 68B and a locking tab 70A and 70B are provided on each handle 66A and 66B along sides thereof opposite to the sides occupied by the indicia. The alignment pins 68A and 68B are preferably substantially cylindrical in shape and project substantially perpendicularly away from the sides of the handles 66A and 66B opposite to the sides thereof on which the indicia are located.

The pins 68A and 68B are dimensioned for insertion into the alignment notches 58A and 58B defined by the ears 56A and 56B when the baskets 44A and 44B are in the closed position. The pins 68A and 68B also preferably have a radius substantially greater than a thickness of the handles 66A and 66B thereby rendering the pins 68A and 68B relatively rigid and inflexible as compared to the handles 66A and 66B. Thus, the notches 58A and 58B and the pins 68A and 68B comprise the alignment means for facilitating alignment of the baskets 44A and 44B with the plate 42 so that the lenses 11A and 11B can be properly maintained within the baskets 44A and 44B when in the closed position.

Locking tabs 70A and 70B are located along edges of the handles 66A and 66B proximate to the distal ends thereof, and project substantially perpendicularly therefrom towards an imaginary vertical line defined by the hinges 54A and 54B. The tabs 70A and 70B are preferably thicker than the handles 66A and 66B so that the tabs 70A and 70B are relatively rigid and inflexibly as compared to the handles 66A and 66B.

Locking notches 72A and 72B are formed in opposite longitudinal edges of the stem 40 at a location for facilitating insertion of the tabs 70A and 70B therein. The notches 72A and 72B recess a certain distance into the stem 40 along opposite surfaces thereof so that the notches 72A and 72B open in directions offset one hundred and eighty degrees from each other. The notches 72A and 72B are also dimensioned for accepting and firmly retaining the tabs 70A and 70B.

Specifically, as illustrated in FIG. 3, when the baskets 44A and 44B are moved towards the closed position, the notch 72B faces the basket 44A and the notch 72A faces the basket 44B. Additionally, as the baskets 44A and 44B are brought nearer the closed position, the tabs 70A and 70B each contact opposite surfaces of the stem 40 adjacent their respective notches 72A and 72B. The handles 66A and 66B are provided with sufficient elasticity and resiliency so that the handles 66A and 66B can be flexed, upon application of an appropriate force, thereby removing the tabs 70A and 70B from engagement with the stem 40 and moving them towards and beyond the opposite surface of the stem 40. It is to be noted that, at this point, the pins 68A and 68B are in the notches 58A and 58B, respectively.

Once the handles 66A and 66B have been flexed sufficiently, the application of the force can cease, thereby allowing the tabs 70A and 70B to move into the locking notches 72A and 72B, respectively, under the influence of forces arising from the resiliency of the handles or extensions 66A and 66B. Once the tabs 70A and 70B are in the notches 72A and 72B, the resiliency of the handles 66A and 66B biases the tabs 70A and 70B against the interior of the notches 72A and 72B, respectively. However, as shown in Figs. 3 and 5, the handles or extensions 66A and 66B remain closed and thus provide a holding force to maintain the baskets 44A and 44B in the closed position.

Accordingly, the tabs 70A and 70B are held within the notches 72A and 72B under the influence of a spring-like force generated by the resiliency of the handles or extensions 66A and 66B. Therefore, the baskets 44A and 44B are locked and firmly maintained in the closed position once the tabs 70A and 70B are in their respective notches 72A and 72B. This insures that the lenses 11A and 11B will be maintained within the baskets 44A and 44B in an appropriate disposition for disinfecting. It is to be noted that to shift the baskets 44A and 44B from the closed to the open position, the above-described process can be reversed.

Because it is desirable to maintain the disinfecting tablets, catalysts or compounds in the reaction chamber 28 while they dissolve or effervesce as required to attain the disinfecting solution-producing reactions, and because gases liberated during effervescence would cause the tablets 29A and 29B to become buoyant and float out of the reaction chamber 28, means for maintaining the disinfecting tablets in the reaction chamber 28 are provided in the form of fins 74A and 74B depending from the lower portion of baskets 44A and 44B. While the fins 74A and 74B comprise a preferred embodiment other structures could be used to overlie the mouth of the reaction chamber 28, or the basket structure could be increased in size. Regardless of the structure employed, the intent is to provide some means to overlie the mouth of the chamber 28 to prevent migration of the tablets 29a or 29b.

The structure of the fins 74A and 74B is best illustrated in FIG. 2. As shown, the fins 74A and 74B extend from bottom-most portion of the baskets 44A and 44B to form a configuration approximating a right angle. In a preferred construction, the fins 74A and 74B extend from the bottommost ribs 64A and 64B along their entire length. Accordingly, the distance between the apexes of the fins 74A and 74B is approximately equal in length to an opening diameter of the reaction chamber 28.

When the basket assembly 14 is properly attached to the cup 12, the fins 74A and 74B extend across a juncture of the bottom portion 26 and the reaction chamber 28. The fins 74A and 74B are thusly able to retain the disinfecting tablets 29A and 29B within the reaction chamber 28 irrespective of buoyant forces occurring due to the tablets dissolving or effervescence. It is to be noted that the fins 74A and 74B do not interfere with disinfecting solution flow, but actually can serve to direct flow of disinfecting solution through the openings 62A and 62B and into the baskets 44A and 44B, thereby facilitating proper disinfection of the lenses 11A and 11B.

With the structure of the lens case 10 being thusly disclosed, the operation and employment thereof will now be discussed. It is to be understood that other structural and functional characteristics of the lens case 10 will become more clear with reference to the following discussion.

To utilize the lens case 10 for disinfection of contact lenses 11A and 11B, the basket assembly 14 is removed from the cup 12 by rotatably disengaging the threads 22 on the basket assembly 14 from the threads 20 on the upper end portion 18 of the cup 12. The baskets 44A and 44B are then shifted into the open position by application of an appropriate force to the extensions or handles 66A and 66B, as described above. The force must have appropriate magnitude and direction to remove the tabs 70A and 70B from their respective notches 72A and 72B, and move those tabs 70A and 70B to the same side of the leg 40 occupied by the hinges 54A and 54B, respectively. The baskets 44A and 44B are now free to pivotally rotate about the hinges 54A and 54B into the open position as illustrated in FIG. 1.

The lenses 11A and 11B are now removed from the wearer's eyes one at a time. As the lenses 11A and 11B are removed, they are cleaned and/or prepared according to manufacturer's instructions. Once a lens 11A or 11B is properly prepared for disinfection, that lens 11A or 11B is placed, concave side down, upon the supports 52A or 52B. Because the radius of the supports 52A and 52B is approximately the same as the radius of curvature of the lenses 11A and 11B, the lenses 11A and 11B are readily accepted on the supports 52A and 52B.

After a lens 11A or 11B is placed on its respective supports 52A or 52B, the basket 44A or 44B is shifted into the closed position by application of an appropriate force, as described above (i.e. reversing the procedure utilized to shift the baskets 44A and 44B into the open position). The lenses 11A and 11B are placed upon their respective supports 52A and 52B so that the right lens is placed upon the supports 52A or 52B associated with the handle 66A or 66B bearing the marking indicia "R." In this way, the wearer will not be confused as to which lens goes in which eye. The alignment means insures that the baskets 44A and 44B will be properly aligned with the plate 42 so that the lenses 11A and 11B will not fall away from the basket assembly 14 during disinfection.

Once this procedure is completed with both lenses 11A and 11B, both lenses 11A and 11B are firmly retained by the baskets 44A and 44B, respectively, and are ready for disinfection. The cup 12 is placed on a suitably planar surface so that the fins 30 can support the cup 12 substantially perpendicularly to the surface, thereby rendering the cup 12 extending substantially vertically with the reaction chamber 28 at the lowest portion thereof.

A predetermined amount of saline solution, or other disinfecting compound, is added to the cup 12. A fill line may be provided on the body 16 of the cup 12 to indicate the level of this predetermined amount. It is to be noted that the predetermined amount of solution and the dimensions of the cup 12 are chosen such that a sufficient amount of dead air space will remain between an upper surface of the solution and the bottom of the cap 32 when the basket assembly 14 is threadibly mated with the cup 12. This dead air space, as stated above, accepts gases liberated by effervescence of the disinfecting tablets so that spillage and spattering thereof is prohibited.

Reactive disinfecting tablets 29A and 29B are now added to the cup 12 by simply dropping them therein. Gravity causes the tablets 29A and 29B to move downwardly and the radiused configurations of the bottom portion 26 and the reaction chamber 28 cooperates with gravitational forces for directing the tablet or tablets into the reaction chamber 28. Because the interior of the cup 12 is smooth, nothing prohibits the tablets from entering the reaction chamber 28.

Once the tablets are in the reaction chamber 28, the basket assembly 14 is threadibly engaged with the cup 12. The basket assembly 14 is rotated until the underside of the flange 36 compressively engages the sealing ridge 24 on the upper end portion 18 of the cup 12. The cooperation of the threads 20 and 22, as well as the compression of the ridge 24 insures that the cup 12 is sealed by the basket assembly 14, thereby preventing spillage and spattering of the disinfecting solution.

When the cup 12 and the basket assembly 14 are properly joined, the fins 74A and 74B on the bottom of the baskets 44A and 44B are located just above and overlie the mouth of the reaction chamber 28. Accordingly, as the disinfecting tablets 29A and 29B begin to effervesce or dissolve, the fins 74A and 74B prevent the tablets 29A and 29B from leaving the reaction chamber 28, thereby insuring that the tablets 29A and 29B remain in the chamber 28 in close proximity so that the desired disinfecting solution-producing reactions can take place. This is important for certain contact lens disinfecting systems which require the tablets 29A and 29B to be held in close proximity to each other as they effervesce or dissolve for providing the proper chemical reactions.

As the tablets 29A and 29B effervesce, any gases liberated thereby move freely upwardly into the substantial dead air space located between the upper surface of the solution and the bottom of the cap 32. Additionally, as the tablets 29A and 29B react, the fins 74A and 74B serve to direct the disinfecting solution formed by the reaction through the openings 62A and 62B and into the baskets 44A and 44B to disinfectingly encounter the lenses 11A and 11B. The slot 50 in the plate 42 also facilitates introduction of the disinfecting solution into the baskets 44A and 44B. Additionally, the apertures 48 and the openings 62A and 62B allow for free flow of disinfecting solution about the lenses 11A and 11B through the baskets 44A and 44B. In this way, the lens case 10 provides for proper disinfection of the lenses 11A and 11B.

Once the disinfection cycle is completed, the lenses 11A and 11B can be removed from the case 10 and worn by the wearer. To remove the lenses 11A and 11B from the case 10, an appropriate torque is applied, facilitated by the protuberances 38, to the cap 32, thereby rotating the basket assembly 14 to remove the threads 20 from the threads 22. As the basket assembly 14 is rotated, the lenses 11A and 11B are aggitated within the disinfecting solution within the cup 12 to insure proper disinfection of the lenses 11A and 11B. This aggitation also promotes proper neutralization of the cleaning and/or disinfecting solutions applied to the lenses 11A and 11B.

After the threads 20 and 22 are disengaged, the basket assembly 14 can be removed from the cup 12. The apertures 48, the slot 50, and the openings 62A and 62B insure proper drainage of the disinfecting solution from the basket assembly 14, thereby preventing contamination of the lenses 11A and 11B, or other disinfecting fluid utilized in a subsequent disinfections of the lenses 11A and 11B. The cup 12 is also drained of disinfecting fluid. Again, because the interior of the cup 12 is substantially smooth, proper drainage thereof is insured.

The baskets 44A and 44B are, in turn, shifted into the open position to allow removal of the lenses 11A and 11B therefrom. Because the lenses 11A and 11B are supported above the plate 42 by the radiused fins 52A and 52B, respectively, the lenses 11A and 11B can be easily removed therefrom. The slot 50 has assured that no appreciable amount fluid remains behind the lenses 11A and 11B, thereby eliminating surface tension which might hold the lenses 11A and 11B sufficiently to render removal thereof difficult. This is an improvement over the lens cases of the prior art wherein the lenses can become relatively firmly attached to the lens case due to surface tension created by the disinfecting fluid disposed about the lenses and often located between the lenses and the case. This surface tension can be quite significant and can lead to increased difficulty in removing lenses from the case. This increased difficulty can result in damage to the lenses, to say nothing of the frustration experienced by the wearer.

While a preferred embodiment of the present invention is shown and described, it is envisioned that those skilled in the art may devise various modifications of the present invention without departing from the spirit and scope of the appended claims. The invention is not intended to be limited by the foregoing disclosure, but only by the following appended claims.

The invention claim is:

1. A contact lens case for use with a single or multi-tablet lens disinfecting or cleaning system, a contact lens case comprising: a cup including a cylindrical main body portion and a bottom surface portion, and lens retaining means for releaseably holding a pair of contact lenses for disposition within the cup; the cup being of dimensions sufficient for holding a predetermined amount of a disinfecting or cleaning solution such that when the lens retaining means is inserted into the cup, said retaining means may be immersed in a solution; and a reaction chamber formed in and depending from the bottom surface portion of the cup, said reaction chamber being of substantially reduced dimensions with respect to said cylindrical main body portion such that said reaction chamber is adapted to retain disinfecting or cleaning tablets in close proximity within said chamber for permitting occurrence of a disinfecting or cleaning solution producing reactions, and said lens retaining means including structure such that when assembled to said cup, said structure is being disposed in close proximity to the reaction chamber to prevent a disinfecting or cleaning tablet from migrating out of said reaction chamber.

2. A contact lens case as defined in claim 1 wherein the walls of the reaction chamber are curved for retaining disinfecting or cleaning tablets therein.

3. A contact lens case as defined in claim 1 wherein the bottom surface portion of said cup is curved for guiding disinfecting or cleaning tablets into the reaction chamber.

4. A contact lens case as defined in claim 1 wherein the cup has an upper end portion bearing a sealing ridge; the lens retaining means comprising a cap; and the sealing ridge being compressible between the upper end portion and the cap.

5. A contact lens case as defined in claim 1 wherein the cup has supporting means for vertically supporting the contact lens case.

6. A contact lens case as defined in claim 5 wherein the supporting means comprises fins depending from at least one of the bottom portion and the reaction chamber.

7. A contact lens case as defined in claim 1 wherein the lens retaining means comprise a basket assembly including a cap and a depending basket structure; the basket structure comprising a stem depending from the cap; a base plate depending from a distal end of the stem; and baskets for releasably holding contact lenses shiftably attached to the plate for shifting between an open position for removing lenses, and a closed position for holding lenses.

8. A contact lens case as defined in claim 7 wherein the base plate includes means for facilitating flow and drainage of disinfecting or cleaning solution.

9. A contact lens case as defined in claim 8 wherein the means for facilitating flow and drainage of disinfecting or cleaning solution comprises a radial slot disposed in the base plate.

10. A contact lens case as defined in claim 7 wherein the baskets are shiftably attached to the base plate by means of integral hinges; and the hinges having a thickness less than a corresponding thickness of the plate.

11. A contact lens case as defined in claim 7 further comprising means for facilitating shifting of the baskets between the open and closed positions and for latching the baskets in the closed position, said means comprising a flexible extension projecting from the baskets.

12. A contact lens case as defined in claim 11 further comprising means for aligning the baskets with the base plate and means for locking the baskets in the closed position.

13. A contact lens case as defined in claim 12 wherein the means for aligning the baskets with the plate comprises an alignment pin and an alignment notch operatively associated with each of the baskets; and the alignment pin being insertable into the alignment notch when the associated basket is in alignment with the base plate in the closed position.

14. A contact lens case as defined in claim 12 wherein the means for locking the baskets in the closed position comprises a locking notch and a locking tab operatively associated with each of the baskets; and the locking tab being insertable into the locking notch when the associated basket is in the closed position.

15. A contact lens case as defined in claim 11, wherein said lens retaining means structure includes one or more fin means depending therefrom which fin means are disposed to overlie said reaction chamber and thereby maintain a tablet therein.

16. A contact lens case for use with a single or multi-tablet lens disinfecting or cleaning system, a contact lens case comprising: a cup member including a cylindrical main body portion and a bottom portion; a lens retaining means for releaseably holding a pair of contact lenses for disposition within the cup; the cup being of dimensions sufficient for holding a predetermined amount of disinfecting or cleaning solution when the lens retaining means is inserted into the cup such that said lens retaining means and any contact lenses housed therein will be immersed in a solution; the bottom portion of said cup being defined by an outer radius portion and a reaction chamber disposed inwardly of said outer radius portion; said reaction chamber having an open end of substantially smaller dimensions than that of said main body portion, said reaction chamber adapted for retaining disinfecting or cleaning tablets in close proximity within said chamber as required for permitting the occurrence of a disinfecting or cleaning solution.

17. A contact lens case comprising: a cup adapted to receive a quantity of disinfecting or cleaning solution; a lens supporting basket assembly mountable to said cup for disposing a pair of lenses in a disinfecting or cleaning solution contained within said cup; said basket assembly comprising an integral molded component including a cap, a stem portion joined to the cap, a base plate joined to the stem portion for supporting one of a pair of lenses on each side thereof and basket means hingedly connected to the base plate at diametrically opposed locations by integral hinges such that the basket means can overlie said base plate on opposite sides in an overlying position thereof to maintain a pair of contact lenses within said basket assembly, and latch means for maintaining said basket means in said overlying position, said latch means comprising a flexible, integral extension formed on each basket means and extending upwardly therefrom and including a tab member on the end therewith which is engageable with said stem portion to maintain the basket means in said overlying position with respect to said base plate, and said stem portion including a notch for receiving said tab member.

18. A contact lens case according to claim 17, further including alignment means for properly aligning said basket means so that said tab member may be disposed in said notch.

19. A contact lens case according to claim 18, wherein said alignment means comprises an alignment pin and an alignment notch formed on said base plate and said basket means respectively, such that said alignment pin is insertable into said alignment notch to align properly said basket means preparatory to engagement of said tab member with said stem.

20. A contact lens case according to claim 17, wherein said cup includes a bottom surface portion with a reaction chamber formed in and depending from the bottom surface portion of said cup, said reaction chamber being of substantially reduced dimension with respect to said cup.

21. A contact lens case comprising: a cup for a quantity of disinfecting or cleaning solution; a lens supporting basket assembly mountable to said cup for disposing a pair of lenses in a disinfecting or cleaning solution contained within said cup; said basket assembly comprising an integral molded component including a cap, a stem portion joined to the cap, a base plate joined to the stem portion for supporting one of a pair of contact lenses on each side thereof, and a pair of basket means hingedly connected to the base plate at diametrically opposed locations by integral hinges such that the basket means can overlie said base plate on opposite sides thereof to maintain a pair of lenses within said basket assembly, latch means in the form of flexible integral extensions formed on each said basket means and extending upwardly therefrom and including tab means on said extensions engageable with said stem portion to maintain the basket means in an overlying position with respect to the base plate, means for aligning the basket means with the base plate preparatory to engagement of the latch means which means for aligning the basket means comprises an alignment pin and an alignment notch formed on said base plate and said basket means such that said alignment pin is insertable into said notch to properly align said basket means preparatory to said engagement of said tab means with said stem portion.

22. A contact lens case according to claim 21, wherein said cup includes a bottom surface portion with a reaction chamber formed in and depending from the bottom surface portion of said cup, said reaction chamber being of substantially reduced dimension with respect to said cup.

* * * * *